(12) United States Patent
Bernhard

(10) Patent No.: US 7,126,352 B2
(45) Date of Patent: Oct. 24, 2006

(54) METHOD AND DEVICE FOR DETERMINING THE MOISTURE CONTENT AND CONDUCTIVITY IN THE GROUND AND IN BULK MATERIALS

(75) Inventor: Ruth Bernhard, Garching (DE)

(73) Assignee: GSF - Forschungszentrum für Umwelt und Gesundheit GmbH, Oberschleissheim (DE)

( * ) Notice: Subject to any disclaimer, the term of this patent is extended or adjusted under 35 U.S.C. 154(b) by 0 days.

(21) Appl. No.: 11/135,780

(22) Filed: May 24, 2005

(65) Prior Publication Data

US 2005/0212532 A1    Sep. 29, 2005

Related U.S. Application Data

(63) Continuation-in-part of application No. PCT/EP03/012040, filed on Oct. 30, 2003.

(30) Foreign Application Priority Data

Nov. 30, 2002    (DE)    ................................ 102 56 064

(51) Int. Cl.
*G01R 27/26*    (2006.01)
(52) U.S. Cl. ........................ 324/664; 324/667; 324/681
(58) Field of Classification Search ................ 324/664, 324/667
See application file for complete search history.

(56) References Cited

U.S. PATENT DOCUMENTS

| | | | |
|---|---|---|---|
| 3,155,899 A | 11/1964 | Davidson | |
| 3,715,656 A | 2/1973 | Hyde et al. | |
| 4,426,616 A | 1/1984 | Maier | |
| 4,616,425 A | 10/1986 | Burns | |
| 4,683,904 A * | 8/1987 | Iltis | 324/667 |
| 5,218,309 A | 6/1993 | Nelson et al. | |
| 5,341,673 A * | 8/1994 | Burns et al. | 324/664 |
| 5,418,466 A | 5/1995 | Watson et al. | |
| 6,904,789 B1 * | 6/2005 | Campbell et al. | 324/664 |

FOREIGN PATENT DOCUMENTS

| | | |
|---|---|---|
| DE | 38 17 504 | 2/1989 |
| EP | 0 552 275 | 7/1998 |

\* cited by examiner

*Primary Examiner*—Anjan Deb
*Assistant Examiner*—Timothy Dole
(74) *Attorney, Agent, or Firm*—Klaus J. Bach

(57) ABSTRACT

In a method and device for determining the moisture content and conductivity in the ground and in bulk materials, a capacitive sensor is disposed in the ground or the bulk material, the sensor is charged from a constant external voltage supply with a given initial current from a given first voltage threshold value to a given second voltage threshold value and either a voltage/time diagram is determined or a first charging time required for charging the sensor from the first to the second voltage threshold values by the constant external voltage supply is determined and a second charging time is determined wherein either the initial current and/or at least one of the two voltage threshold values are altered and the water content and the conductivity are determined by verification of the two charging times or of the voltage/time diagram.

5 Claims, 6 Drawing Sheets

METHOD AND DEVICE FOR DETERMINING THE MOISTURE CONTENT AND CONDUCTIVITY IN THE GROUND AND IN BULK MATERIALS

This is a Continuation-In-Part application of International Application PCT/EP2003/012040 filed Oct. 30, 2003 and claiming the priority of German application 102 56 064.1 filed Nov. 30, 2002.

BACKGROUND OF THE INVENTION

The invention resides in a method and a device for determining the moisture content and conductivity in the ground and in bulk materials by way of a capacitive sensor introduced into the ground or the bulk material which is charged by a voltage and determining the time required for the charging of the sensor.

As a reliable measure for determining the moisture content in a soil sample or a bulk material the dielectric constant $\epsilon_m$ between two electrodes is used. In comparison with many other materials water has a very high dielectric constant so that already a small moisture content of the measuring volume that is in the soil sample or in the bulk material results in a significant change of the dielectric constant $\epsilon_m$. Typical areas of application include particularly the surveillance of the ground as well as the quality control of agricultural products (for example, flour, legumes and soya but generally also in the production and transportation of moisture-sensitive goods such as sugar.

In the determination of the moisture content of a bulk material or the ground by way of the dielectric constant $\epsilon_m$ the additional determination of the conductivity is easily possible. The electric conductivity of a material can be used for determining the presence of contaminations which noticeably influence the electric conductivity or resistance of the moist material.

Therefore the measurement of the dielectric constant $\epsilon_m$ and the conductivity of a bulk material or ground area is suitable not only for a determination of the moisture content but also for determining impurities dissolved in the water.

The following methods for the determination of the dielectric constant $\epsilon_m$ and at the second time the conductivity $\sigma_m$ in materials are known for a characterization of soils and bulk materials:

In the so-called TDR method [1] travel differences along a wave conductor (TDR probe) are utilized which generally change with the moisture content in the material around the wave conductor. The impulse passes through one wave conductor while a second wave conductor serves as reference mass. From a measured pulse speed, the dielectric constant is calculated and subsequently the moisture content $\Theta$ of the material is calculated. An increase of the dielectric constant results in a decrease of the pulse speed. The relationship between $\epsilon_m$ and $\Theta$ must be assumed to be known. For the operation and the registration of the TDR signal a cable tester is needed which must have a resolution of several 4 GHz up to more than 100 GHz depending on the required time resolution.

[2] describes additionally the determination of the conductivity $\sigma_m$.

The evaluation of a TDR signal is difficult. The cable tester required and an evaluation unit with the required resolution capability for travel time measurements needed in connection therewith is very expensive.

Alternatively, in [3] a capacity measurement method is proposed which utilizes an electromagnetic oscillation circuit for determining the dielectric constant $\epsilon_m$ of the material, which is essentially less expensive than the TDR method. In this case, a sensor is provided in the form of a condenser with two condenser electrodes connected to an oscillator. An oscillator, an analog electronic circuit, generates a sinus-shaped output signal whose frequency $f_{osz}$ is determined by the capacity of the sensor $C_3$, but also by other components, particularly the required inductivity L for the oscillator. The relationship is as follows:

$$f_{osz} = \sqrt{LC_3} = 1/\sqrt{L\epsilon_m C_a} \qquad (1)$$

A higher dielectric constant is consequently apparent from a lower $f_{osz}$:

The frequency can be determined exactly, safely and inexpensively with simple means. In this way, also accurate determinations of dielectric constants are possible by this method.

The frequency $f_{cso}$ generally is dependent on the conductivity of the material being examined wherein an increasing conductivity generally results in lower frequencies. A higher dielectric constant is simulated in this way. However, this influence of the conductivity becomes smaller with increasing frequency. For determining the dielectric constant therefore preferably high measuring frequencies are used. Although, the influence of the conductivity is reduced thereby, it still remains.

For a common determination of the dielectric constant $\epsilon_m$ and the conductivity $\sigma_m$ of a material, the sensor can therefore be considered to be a complex resistor in a substitute circuit. For the determination of the complex resistance with a real and an imaginary component again a network channel analyzer is required which increases the expenses for a simultaneous determination of the moisture content and the conductivity.

It is the object of the present invention to provide a method and an apparatus for performing a method of determining the moisture content and the conductivity in soils and in bulk materials in a relatively simple and inexpensive way.

SUMMARY OF THE INVENTION

In a method and device for determining the moisture content and conductivity in the ground and in bulk materials, a capacitive sensor is disposed in the ground or the bulk material, the sensor is charged from a constant external voltage supply with a given initial current from a given first voltage threshold value to a given second voltage threshold value and either a voltage/time diagram is determined or a first charging time required for charging the sensor from the first to the second voltage threshold values by the constant external voltage supply is determined and a second charging time is determined wherein either the initial current and/or at least one of the two voltage threshold values are altered and the water content and the conductivity are determined by verification of the two charging times or of the voltage/time diagram.

If only the charging times are recorded on the basis of two different sets of parameters which differ in the voltage threshold values and/or the start-out circuit, each of the two charging times can be determined redundantly by a periodic charging and discharging of the sensor, and possible disturbances can be eliminated by averaging the individual charging times. If an upper and a lower threshold value is used in each case as an initial trigger for a discharging or charging procedure for the sensor the period of the measuring signal is composed of the charging and discharging time of the sensor. The period of the measuring signal is generated from the charging and discharging times of the sensor, wherein the charging time can be determined with a known discharging behavior in a particularly advantageous manner by a simple and accurate measurement of the frequency of the periodic charging and discharging. The two frequencies of the two periodic measurement signals are also used for the determination of the moisture content and the conductivity.

For the recording of the measuring signal, that is, the voltage-time-diagram of the periodic measurement signals or the charging times, a storage oscilloscope, a transient recorder or a rapid measuring data recording card may be used which transfers the recorded data to a processor or a PC for further evaluation.

Preferred embodiments of the invention will be described below on the basis of the accompanying drawings.

DESCRIPTION OF PREFERRED EMBODIMENTS

Figure 1:
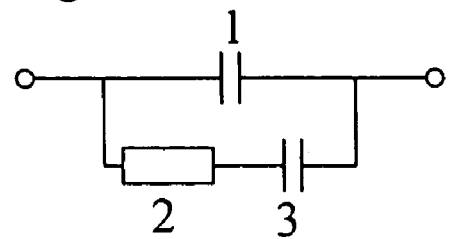
FIG. 1 shows a basic substitute circuit of the sensor.

FIG. 1 shows the substitute circuit of the sensor in a soil segment or in a bulk material.

Basically, the conductivity $\sigma_m$ of a material can be represented by a resistance $R_s$ which is arranged parallel to $C_s$. $R_s$ and $\sigma_m$ have the relationship, $$R_s = G/\sigma_m \quad (2)$$

wherein G is a constant geometry-dependent factor of the sensor which can be determined by a calibration measurement.

With their large dipole moments which align themselves in a magnetic field, water molecules affect the dielectric constant of a material $\epsilon_w$ to a large degree. The electric conductivity in the water is furthermore not a metallic conductivity with movable charges and an opposite charge at the stationary phase, but an ionic conductivity. That means that the electric field applied separates the charges because of the conductivity present as much as possible and pulls them further apart so that a dipole is induced. The dipoles drift apart until the electric field of the separated ions formed thereby compensates for the applied outer field.

This effect of the water molecules in the form of dipoles is represented in the substitute circuit according to FIG. 1 by the condenser 1 with the capacity:

$$C_w = \epsilon_m C_a \quad (3)$$

(dielectric constant $\epsilon_m$, capacity in air Ca). In this case, $C_a$ is the capacity of the sensor 1 or, respectively, the capacity of the insulation, if insulated electrodes are used and air is in the intermediate space. If a material with a dielectric constant $\epsilon_m$ is disposed in the intermediate space, the total capacity in the equation (2) is increased. Parallel thereto is a series circuit consisting of the ion resistance 2 with an ohmic resistance $R_s = G/\sigma_m$ (equation (2)) and another condenser 3 with a capacity $$C_{ion} = \epsilon_{ion} C_a \quad (4)$$

which represents the effect of the ion separation, wherein $\epsilon_{ion}$ is given by a function of $\sigma_m$;

$$\epsilon_{ion} = g(\sigma_m) \quad (5)$$

In a first approximation, there is the relationship:

$$\epsilon_{ion} = \alpha \sigma_m \quad (6)$$

wherein $\alpha$ must be determined as a material constant for a soil to be examined or for a bulk material. $\alpha$ interconnects the two values $R_s$ and $C_{ion}$, so that, in addition to $C_s$, only one additional value needs to be determined, that is $R_s$.

Figure 2:
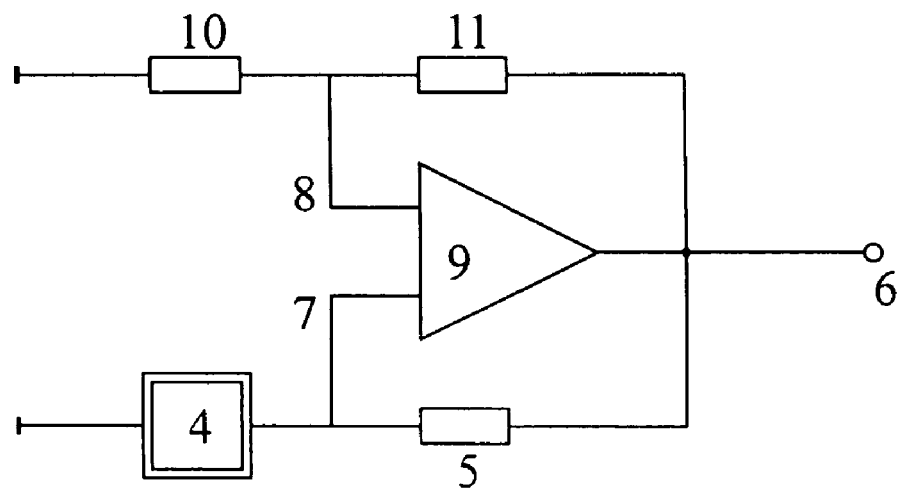
FIG. 2 shows the arrangement of the apparatus in principle.

FIG. 2 shows the main setup of the arrangement with a multi-vibrator circuit for determining the moisture content and the conductivity in a simplified circuit. The sensor 4 forms, together with the operating resistance $R_a$ 5, an RC-member which determines essentially the time constant and, consequently, the frequency of the circuit. The multi-vibrator circuit consists essentially of an operational amplifier as an active element 9 which is connected at one side with a signal output 6 to an operational resistor 5 and the part of the voltage divider (resistor 11), while the other side picks up the voltage 7 between the sensor 4 and the operational resistor 5 and the voltage 8 between two additional resistors 10 and 11 (voltage divider) The time dependency of the charge curve (voltage 7) at the sensor 4 is determined by the capacity of the sensor, the resistance $R_a$ 5 and further specification of the circuit and the sensor. When the voltage 7 at the sensor 4 reaches a certain threshold voltage $U_{s1}$, the active element 9 switches and the sensor 4 is discharged. In this state, the voltage 6 changes to another known value $U_2$. Upon reaching a lower, that is, a second threshold voltage $U_{s2}$, the discharge is terminated, the active element is again switched back and the sensor is again charged. The output signal 6 is therefore a digital rectangular signal. With a small sensor capacity, the charging and discharging procedures are faster and the output signal has a higher frequency.

In this arrangement, first the dielectric constant $\epsilon_m$ of a material is determined using the capacity method with the aid of the multi-vibrator circuit, wherein the sensor 4 with the capacity $C_s$ is charged by way of a resistor $R_a$ 5 and is again discharged when a certain voltage has been reached. A periodic charging and discharging results in a signal series with a frequency f, wherein the time constant is determined by the RC member with $R_a$ and $C_s$. The frequency f generated:

$$f = h(R_a, C_2) \quad (7)$$

is consequently influenced by the resistance and the capacity of the RC-member, wherein an increasing dielectric constant results in a decreasing frequency f. In this way, a digital signal is directly generated which is less sensitive to disturbances and with which also the frequency can be determined in a simple manner. Furthermore, the circuit does not need an inductivity L which also can be disturbed from the outside.

However, an accurate analysis shows that, also in this case, the frequency f is influenced by the conductivity $\sigma_m$ of the material. The frequency f drops when $\sigma_m$ of the material increases. The decisive point of this dependency is no longer the frequency like it is in connection with oscillators, but the resistance $R_s$, which, like above, is determined by the conductivity of the material and which is parallel to the sensor condenser $C_s$ and which causes $C_s$ to be charged to a lesser degree but instead the condenser $C_{ion}$ 3 arranged in a series circuit (FIG. 1) is charged. An increase in the conductivity results in a lower $R_s$ and also in a lower frequency. But it is not clear whether a lower frequency is caused by an increase of the dielectric constant or an increase in the conductivity. An increased conductivity consequently can simulate, or mislead to the assumption of, a higher dielectric constant. Only if:

$$R_a << R_s \qquad (8)$$

can the frequency be taken to be independent of the conductivity. A smaller operating resistance $R_a$ however results with a predetermined sensor capacity in a high frequency. With predetermined specifications of the sensor this condition cannot be fulfilled with the presently available electronic components since measurements for determining $C_s$ and, consequently, $\epsilon_m$ are not absolutely accurate.

For a simultaneous determination of the dielectric constant $\epsilon_m$ and the conductivity am the arrangement of FIG. 2 must be modified. The modifications relate to additional electric circuitry of the digital multi-vibrator circuit, by which certain electric properties $E_i$ can by modified. The determination occurs with measurements with various settings $E_i$ for the same examination object, wherein several frequencies $f_i$ are provided. From these frequencies, the properties of the material $\epsilon_m$ and $\sigma_m$ can then be calculated.

The equipment expenses are low in comparison with the TDR method which uses expensive cable testers or the capacitance method with an expensive network analyzer. Accurate frequency measurements can be reliably achieved with comparatively simple means. A measurement with two settings $E_1$ and $E_2$ that is a determination of two frequencies $f_1$ and $f_2$ is fully sufficient for achieving the object.

Figure 3:
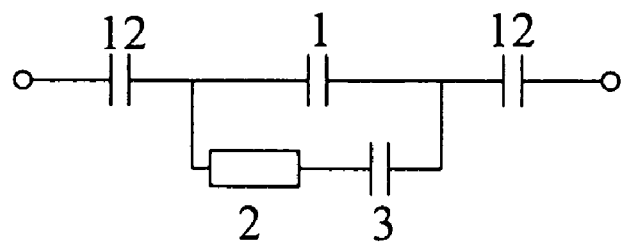
FIG. 3 shows a substitute circuit of the sensor with isolated electrodes for a dielectricum with high conductivity.

As described in connection with FIG. 1, the sensor 4 corresponds to a parallel circuit of the actual sensor capacitance $C_s$1 and the series circuit of the resistor $R_s$2 and the condenser $C_{ion}$3, which is determined by the conductivity $\sigma_m$ of the material. These electrodes of the sensor capacitance 1 must be isolated if the material has a high conductivity. In the substitute circuit this isolation results in a series arrangement of two additional condensers $C_i$ 12 (see FIG. 3. The component provided in addition to the actual sensor capacitance $C_s$ 1, that is the resistors 2, the condenser $C_{ion}$ 3 and the 12, significantly affect the time curve of the charging and discharging procedure and consequently the frequency of the output signal 6.

By modifications of the circuit of FIG. 2, the values of $C_s$ 1 and $R_s$ 2 can now be determined together with $C_{ion}$. Consequently, in accordance with the equations (3) and (2) $\epsilon_m$ and $\sigma_m$ of a material can be determined at the same time.

Below two embodiments of the arrangement for determining the moisture content and the conductivity in soils and in bulk materials but also in other materials will be described, each of them including an appropriate modification.

Figure 4A:
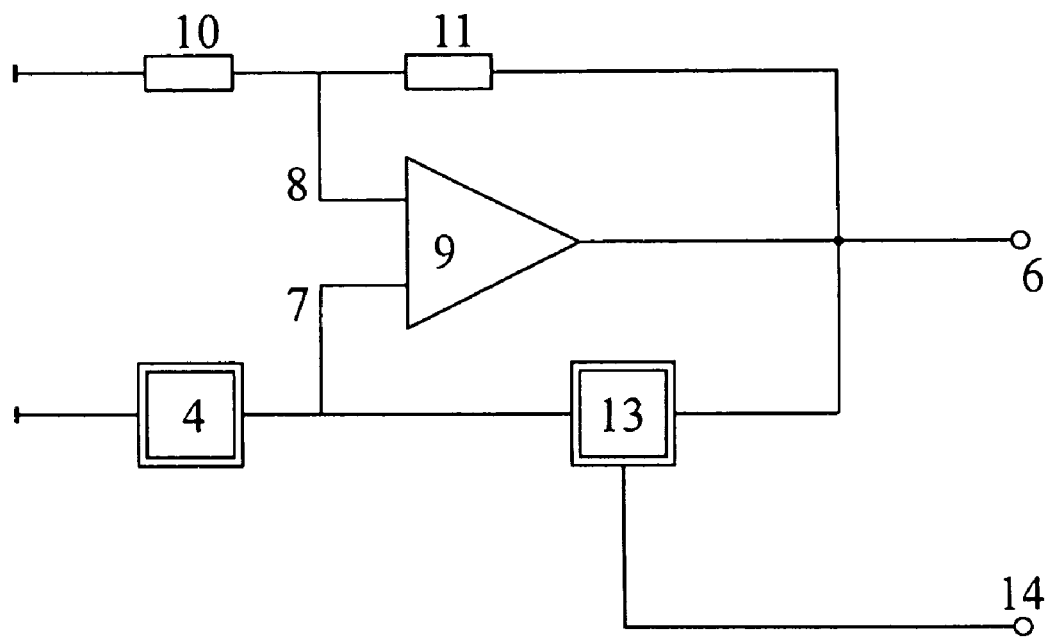
FIGS. 4a and 4b show a simplified circuit of the apparatus in a first embodiment including an controllable resistor 13 in the sensor branch.
Figure 4B:
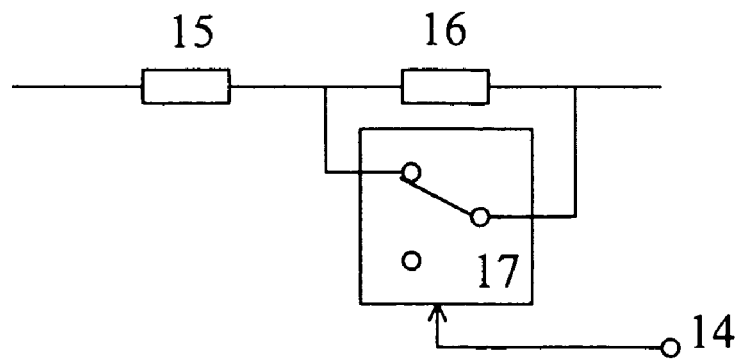

The first embodiment is shown in FIGS. 4a and 4b. The resistor $R_a$ 5 according to FIG. 2 is replaced in FIG. 4 by a switchable resistor 13 with two switch positions. This switchable resistor 13 consists of two serially arranged resistors 15 and 16 and a switch 17 which is controllable by a signal HL 14 and includes two switch positions wherein, in one switch position, the resistor 16 is bridged (see FIG. 4b). The switchable resistor 13 therefore represents, depending on the switch position, two different pre-resistances, that is, either a resistance $R_{a1}$ corresponding to the resistor 15 or a resistance $R_{a2}$ corresponding to the sum of the resistors 15 and 16. Consequently, two different resistances can be established. The influences of $R_{a1}$ and $R_{a2}$ to the charging and discharging procedures are significantly different and result, with the same sensor arrangement and the same material, in different frequencies $f_1$ and $f_2$.

Figure 5A:
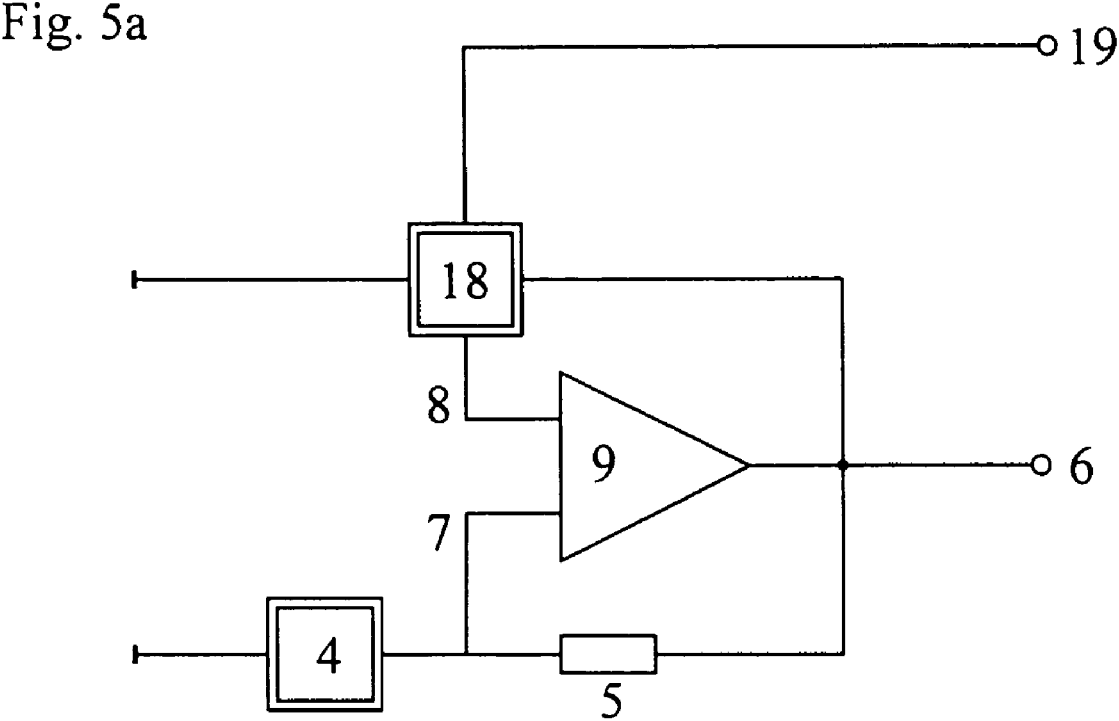
FIGS. 5a and 5b show simplified circuits of the apparatus in a second embodiment including a resistor arrangement in a reference branch, that is, in the voltage control branch.
Figure 5B:
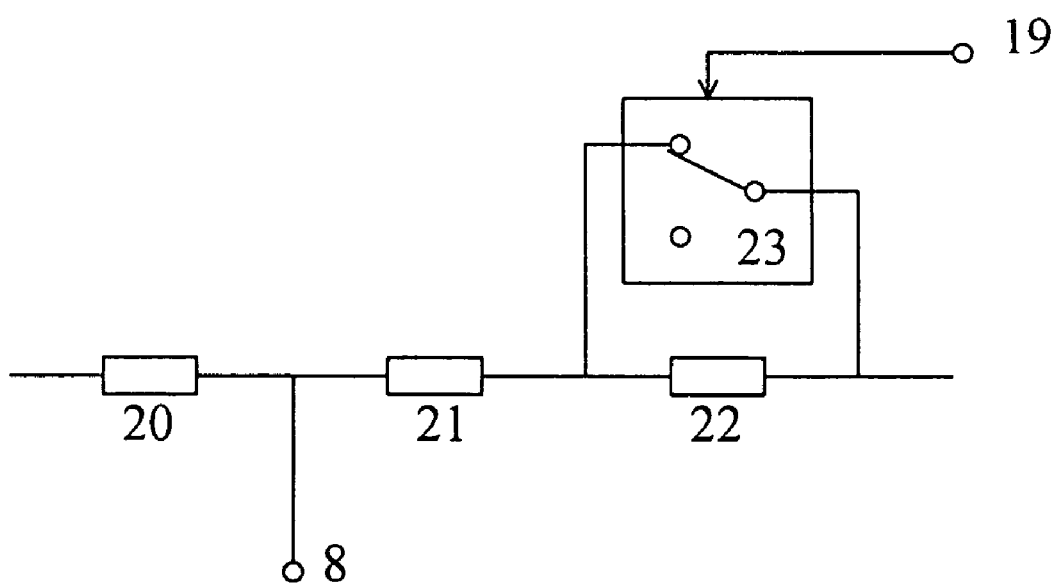

The alternative second embodiment is shown in FIGS. 5a and 5b. It differs from the first embodiment in that by the modification of the circuit not the charge current, but the lower and upper voltage threshold values at the sensor can be changed. The resistors 10 and 11, which in the base circuit according to FIG. 2 as voltage dividers determine in the form of the signal 8, the threshold voltages $U_{s1}$ and $U_{s2}$ for the switching over of the active element, have been replaced by a resistance circuit 18. The resistor 20 corresponds therefore to the resistor 10 of FIG. 2 whereas the resistor 11 of the resistance circuit is replaced by a series arrangement of the resistors 21 and 22, wherein the resistor 22 can be bypassed by a switch 23 under the control of a switching signal 19.

A circuit according to FIG. 4a or 5a is calibrated by an exchange of components of the sensor 4, that is, by condensers $C_j$ (j=1-n) with known capacity instead of the condenser capacity $C_s$ 1 and with resistors $R_k$ (k=1 . . . m) instead of the resistor $R_s$2 and dependent thereon conductors $C_n$ for $C_{ion}$ 3. With a calibration with known capacities $C_j$ and known resistances $R_k$ calibration functions are obtained:

$$F_{1,2} = g_{1,2}(C_j, R_k) \qquad (9)$$

Figure 6:
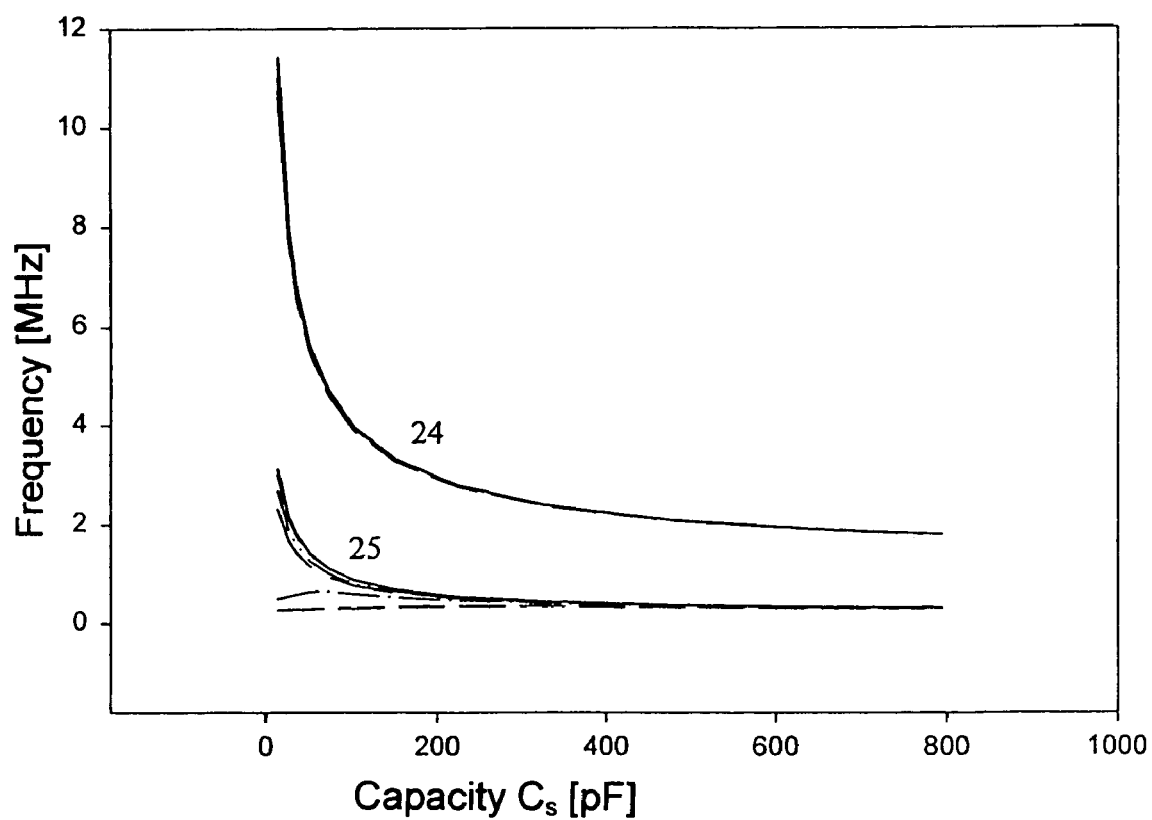
FIG. 6 shows the frequency signal obtained depending on the sensor capacity.

These functions, shown for example in FIG. 6 as frequency f in MHz over the capacitance $C_s$ in pF in a diagram, characterize the switching properties. The set of curves 24 shows the operation with a small operating resistor $R_{a1}$, wherein the capacitance $C_s$ is varied corresponding to the horizontal x-axis up to 800 pF and the conductance of $R_s$ is varied between 0 and 470 µS. The set of curves 24 is reduced in FIG. 6 to a curve which indicates that the conductance of $R_s$ has no significant influence on the function. The set of curves 25 in contrast shows a comparable measurement but with different capacity and a resistance $R_{a2}$ which has a value of about 6 times $R_{a1}$. In this case, the function is disposed on the diagram, that is, the influence of $R_s$ on the frequency is clearly recognizable. The functions (9) are such that, with measured frequencies $f_1$ and $f_2$, the values $C_s$ and $R_s$ can be calculated and, as a result, the material properties $\epsilon_m$ and $\sigma_m$ can be determined.

Figure 7A:
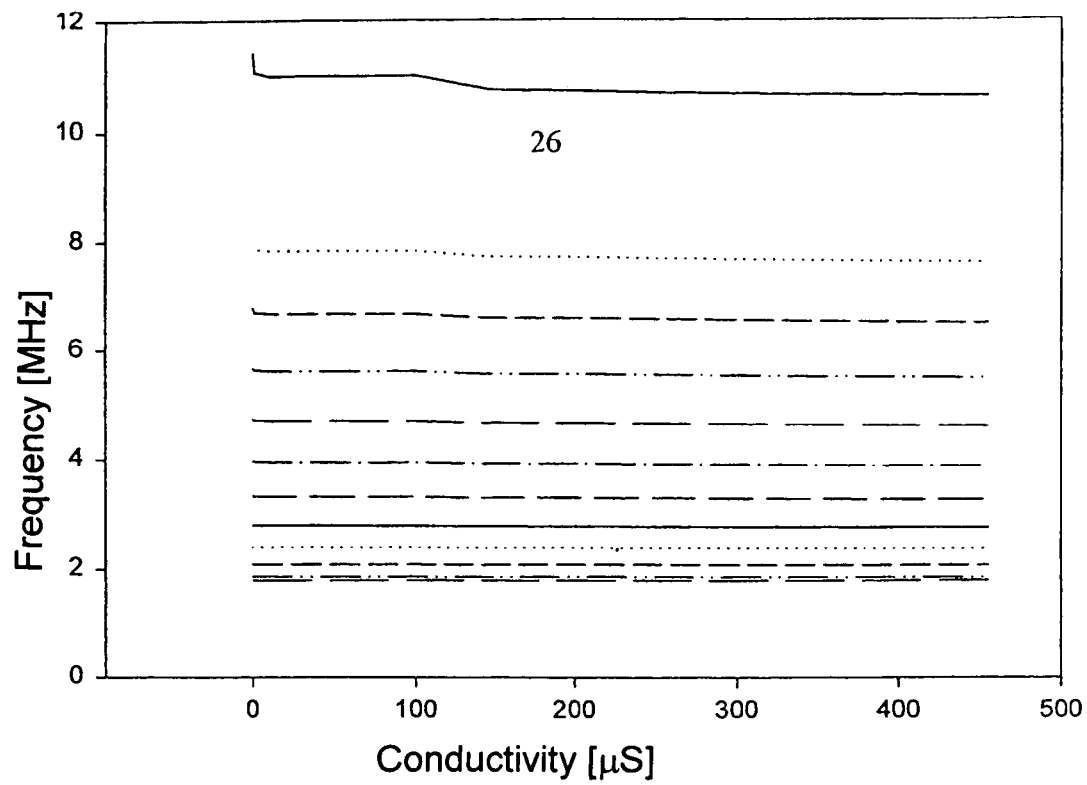
FIGS. 7a and 7b show the frequencies determined dependent on the conductivity of the soil or the bulk material.
Figure 7B:
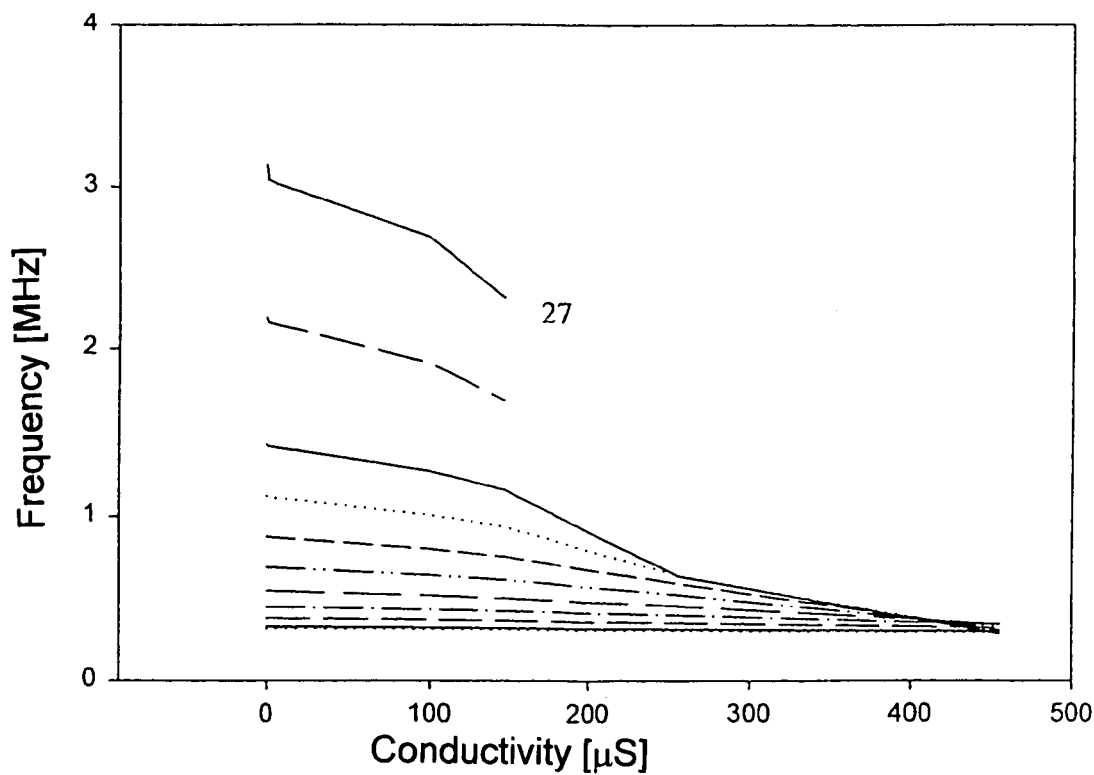

FIGS. 7a and b show the data of the set of curves 24 and 25 plotted as frequency f in MHz (vertical y-axis) over the conductivity in µS (horizontal x-axis). The depicted sets of curves 26 and 27 represent the measuring results with different capacitances $C_s$. The set of curves 26, determined on the basis of a small resistance $R_{a1}$, extends almost horizontally, that is, there is almost no dependency of $R_s$ and, respectively, $\sigma_m$. If, however, the earlier mentioned larger operating resistance in accordance with $R_{a2}$ is introduced a significant dependency of $R_s$ can be observed which also depends on the capacity $C_s$.

The influence of the values $C_s$, $R_s$ and $C_{ion}$ on the frequency of the circuit is obvious from the given relationships and is provided by the function $g_{1,2}$ ($C_j$, $R_k$) given earlier.

For the actual measurement of soils or bulk materials, this relationship is to be used as a reverse function for the determination of the values $C_s$ and $R_s$ from $f_1$ and $f_2$. For a calibration, the resistors $R_{a1}$ and $R_{a2}$ are dimensioned depending on the ratios of these real measurements. In this respect, $R_{a1}$ is to be selected as small as possible. This value is also to be adapted to the maximally possible current, which the active element 9 can generate. With a given material in a first approximation, an average conductivity is to be assumed for the actual measurement. With this setup of the sensor, the geometry factor G is set by the equation (2) so that from the earlier determined conductivity value, an average value for $R_s$ is obtained. For a calibration, the value $R_{a2}$ should correspond as much as possible to this average value $R_s$.

Figure 8:
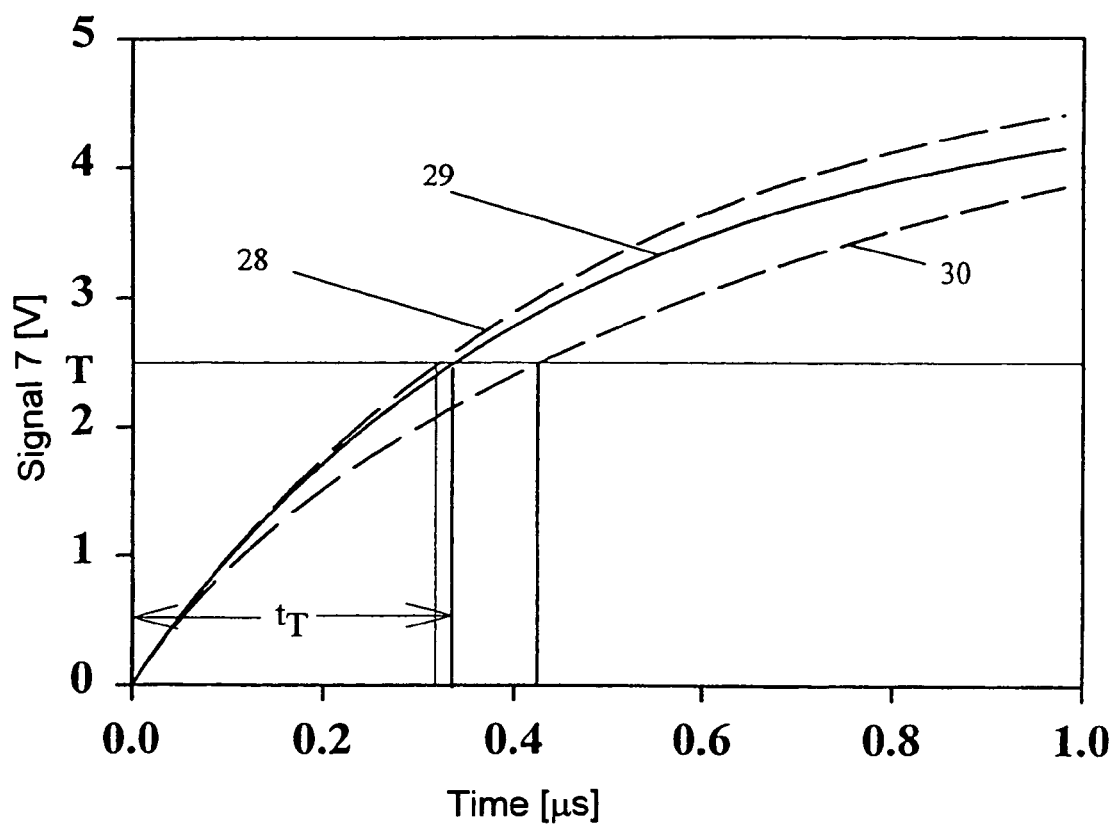
FIG. 8 shows several charge curves with an upper threshold value T in a voltage-time diagram.

FIG. 8 shows several charging curves in time-dependent form of the signal 7 in V (vertical y-axis) over time in μs (horizontal x-axis). Furthermore, a threshold voltage is provided as a horizontal line with the voltage value T. The curve 28 indicates the time-dependent value at $C_s$=80 pF and with a conductivity O (resistance $R_s$ being infinitely large). The curves 29 and 30 correspond to the same capacitance $C_s$, but not the resistances $R_s$=4 kΩ or, respectively, 40 Ω. Each of these curves reaches, after a period represented in the diagram as $t_T$, the voltage threshold value T. All three curves 28, 29 30 show in the lower area an almost identical start-out configuration but, at higher voltages, have clearly different inclinations. As a result, particularly in the embodiments according to FIGS. 4a and 4b, the initially mentioned frequency which is composed of periodically subsequent charging and discharging procedures is influenced by the resistor $R_s$ with increasing level of the voltage value T as threshold voltage for a break up of the charging procedure.

$C_s$ and $R_s$, and with a known α of $C_{ion}$, can be determined therefore in accordance with the two following methods:

In the first method, the sensor circuit is calibrated by an integration of the calibration capacitances $C_{s,k}$ and $C_{ion,k}$ and -resistances $R_{s,k}$ into the circuit and the determination of the respective frequencies $f_{1,k}$ and $f_{2,k}$. The measured frequencies $f_1$ and $f_2$ can then be associated on the basis of table values and if necessary linear interpolations of optimized values for $C_s$ and $R_s$.

The second method is based on the course of the curve of a charging procedure (see FIG. 8). Using a linearly coupled differential equation, a curve according to FIG. 8 can be mathematically defined and, with a known threshold voltage, the respective frequencies $f_1$ and $f_2$ can be determined. With a Fit-procedure, the values for $C_s$ and $R_s$ can then be determined.

In an actual application, in the second method, a sensor is immersed into de-ionized water with a conductivity of 1 μS/cm (case d) and into normal tap water with a conductivity of 540 μS/cm (case n), wherein the conductivities have been determined in a conventional apparatus in accordance with the state of the art at a measuring frequency of 400 Hz. The frequencies $f_1$ and $f_2$ are determined in the case d as $f_{1d}$=1.542 MHz and $f_{2d}$=2.627 MHz, for the case n as $f_{1n}$=1.257 MHz and $f_{2n}$=2.216 MHz. It is apparent that the different conductivities influence the frequencies. With the second method described above the following values are determined: $C_{w,d}$=47 pF, $C_{w,n}$=48 pF, $L_d$=1072 Ω, $L_n$=1709 Ω, $C_{ion,d}$=129 pF and $C_{ion,n}$=205 pF, wherein the coupling coefficient α=0.12. This shows that the values concerning the effect of the water molecules, indicated by the capacitance $C_w$ are almost the same and the conductivities $L_d$ change according to the measurement with another method. In this connection, however, it is to be taken into consideration that the conductivities measured by the two methods are not linearly related. This is caused by the fact that the conductivities were measured at 400 Hz and the method described operates at 2 MHz.

The charging curves according to FIG. 8 are verified for the determination of the moisture content and the conductivity by recording them using a transient recorder or another data storage device for evaluation.

This occurs on one hand by a calculation of a charging curve with a differential equation system and a comparison with the measured curves. Upon occurrence of a deviation, the input value $C_s$ as well as the input value $R_s$ are changed (Fit procedure). Only when the measured and calculated curves coincide, are the respective values for $C_s$ and $R_s$ utilized in order to calculate the values $\epsilon_m$ and σ by means of the equations 3 and 2.

Alternatively, the dielectric constants $\epsilon_m$ of the material and the conductivity σ can be obtained from two settings $E_1$ and $E_2$ that is by way of the two frequencies $f_1$ and $f_2$ representing-two charging times. Here too, the charging curve is calculated using the differential equation system for both $E_1$ and $E_2$, determining the respective frequencies with the threshold value T, and comparing them with $f_1$ and $f_2$. Upon occurrence of a deviation, the input values $C_s$ and $R_s$ are again changed for a new comparison. This Fit procedure is repeated until the calculated and the measured frequencies are essentially equal that is within a predetermined tolerance range.

In a simple procedure, the measured frequencies are compared with the calibration values $f_{1,2}$=$g_{1,2}$ ($C_j$, $R_k$) (equation 9) and the respective values $C_s$ and $R_s$ are determined, if needed, by an interpolation. In accordance with the equations (3) and (2), the values $\epsilon_m$ and σ are then calculated.

As capacitive sensors for determining the moisture content and the conductivity with the earlier mentioned devices and methods the following structures are suitable:

Sensors using for each electrode an insulated wire are particularly suitable for the depth-based measurement of the moisture content of the soil. Ideally, each of the two wires comprises several sections which extend parallel to one another and are arranged in a plane in such a way that each section of an electrode is disposed adjacent two sections of the other electrode. The resulting planar area and the sensitive thickness which depends among others on the wire distance, determines the sensitive volume for the sensor.

Sensors consisting of two insulated plates which are introduced parallel to each other into the ground in an upright position are preferably used when the depth analysis is of no consideration. With the vertical installation of the plates, the disturbances of the sensor to the water movement in the ground is minimized.

For the use in bulk material sensors consisting of two or several rigid insulated electrodes which are inserted into the material are particularly suitable. This arrangement of the electrodes in the bulk material corresponds essentially to that of a TDR probe of the state of the art.

LITERATURE

[1] Topp, G. C., J. L. Davis, and A. P. Annan. 1980. Electromagnetic determination of soil water content: measurement in coaxial transmission lines. Water Resour. Res. 16: 574–582.

[2] Dalton, F. N., W. N. Herkelrath, D. S. Rawlins, and J. D. Rhoades. 1984. Time domain reflectometry: simultaneous measurement of soil water content and electrical conductivity with single probe. Science 224: 989–990.

[3] Eller, H. and A. Denroth. 1996. A capacitive soil moisture sensor. J. Hydrology 185: 137–146.

What is claimed is:

1. A method for determining the moisture content and conductivity in the ground and in bulk materials, comprising the following steps:
   a) introducing a capacitive sensor into the ground or the bulk material,
   b) charging the sensor from a constant voltage supply by means of a predetermined initial current from a predetermined first voltage threshold value up to a predetermined second voltage threshold value and determining one of a voltage-time-diagram and the needed first charging time required for the charging from the first voltage threshold value to the second voltage threshold value, and charging the sensor with the constant voltage supply for determining a second charging time, wherein at least one of the initial current and one of the two voltage threshold values are changed,
   c) determining the moisture content and the conductivity by verification of the two charging times, wherein for each of the two charging times a periodic measuring signal with a particular frequency is generated, with one period of the measuring signal comprising the charging and discharging of the sensor and the frequencies of the two periodic measuring signals are also employed in the determination of the moisture content and the conductivity or the voltage-time-diagram by a comparison of a recorded voltage curve with a solution of a corresponding differential equation system.

2. A method according to claim 1, wherein, for recording the voltage-time-diagram, a transient recorder is used.

3. An arrangement for determining the moisture content and the conductivity in the ground and in bulk material, comprising:
   a) a capacitive sensor arranged in series with a pre-resistor for providing an initial current,
   b) a voltage divider arranged in a parallel circuit with the pre-resistor and including at least two resistors and an output disposed between the two resistors for setting a voltage threshold value, and
   c) an operational amplifier with two inputs and an output and with a constant voltage source wherein, for back-coupling, a part of the voltage divider and the pre-resistor is connected to the two inputs and the output of the operational amplifier, and a sensor and the rest of the voltage divider are connected between the two inputs and ground, at least one of the pre-resistor and one of the two resistors of the voltage divider being switchable back and forth between two resistance values for generating different measurement values.

4. An apparatus according to claim 3, wherein the pre-resistor is switchable back and forth between two resistance values.

5. An apparatus according to claim 3, wherein a resistance of the voltage divider is switchable back and forth between two resistance values.

* * * * *